(12) United States Patent
Moore et al.

(10) Patent No.: US 9,663,443 B2
(45) Date of Patent: *May 30, 2017

(54) PROCESS FOR MAKING TERTIARY AMINOALCOHOL COMPOUNDS

(75) Inventors: David W. Moore, Hebron, IL (US); Christian Spieker, Ibbenbueren (DE); John D. Gummere, Monroe, LA (US)

(73) Assignee: ANGUS CHEMICAL COMPANY, Buffalo Grove, IL (US)

(*) Notice: Subject to any disclaimer, the term of this patent is extended or adjusted under 35 U.S.C. 154(b) by 503 days.

This patent is subject to a terminal disclaimer.

(21) Appl. No.: 14/233,328

(22) PCT Filed: Jul. 16, 2012

(86) PCT No.: PCT/US2012/046855
§ 371 (c)(1),
(2), (4) Date: Jan. 16, 2014

(87) PCT Pub. No.: WO2013/012777
PCT Pub. Date: Jan. 24, 2013

(65) Prior Publication Data
US 2014/0145108 A1 May 29, 2014

Related U.S. Application Data

(60) Provisional application No. 61/509,937, filed on Jul. 20, 2011.

(51) Int. Cl.
| C07C 201/12 | (2006.01) |
| C07C 213/06 | (2006.01) |
| C07C 213/02 | (2006.01) |
| C07C 45/55 | (2006.01) |

(52) U.S. Cl.
CPC ............ *C07C 201/12* (2013.01); *C07C 45/55* (2013.01); *C07C 213/02* (2013.01); *C07C 213/06* (2013.01)

(58) Field of Classification Search
CPC .................................................. C07C 213/06
See application file for complete search history.

(56) References Cited

U.S. PATENT DOCUMENTS

| 4,067,905 A | 1/1978 | Adrian et al. |
| 8,674,139 B2* | 3/2014 | Moore ............... C07C 213/00 564/448 |
| 2011/0105804 A1 | 5/2011 | Major et al. |

FOREIGN PATENT DOCUMENTS

| CN | 101307074 A | 11/2008 |
| GB | 730 602 A | 5/1955 |
| GB | 1 056 589 A | 1/1967 |
| WO | 97/00900 A1 | 1/1997 |
| WO | WO-2009/129099 | 10/2009 |

OTHER PUBLICATIONS

Office Action issued on Japanese Application 2014-521687, mailed Dec. 8, 2015.
First Office Action on Chinese Application 201280041195.3, mailed Nov. 4, 2014.
Wheatly, William B., "alpha,apha-DimethIcholine: Esters and Carbamates" Journal of the American Chemical Society (1954), vol. 76, pp. 2832-2834.
Jones, J.K.N. et al., "378. Reactions of Nitroparaffins. Part II. The reaction of 2-nitropropane with formadehyde and ammonia" Journal of the Chemical Society(1949), pp. 1766-1767.
Klein, Gunter, et al., "Activation of nitroaldol reactions by diethylzine and amino alcohols or diamines as promoters" Tetrahedron Letters (2002), vol. 43(42), pp. 7503-7506.
Luzzio, Frederick A., "The Henry reaction : recent examples" Tetrahedron (2001), vol. 57(6), pp. 915-945.
The International Preliminary Report on Patentability for PCT/US2012/046855 dated Jan. 30, 2014.
Office Action issued on Japanese Application 2014-521687, mailed Aug. 9, 2016.

* cited by examiner

*Primary Examiner* — Peter F Godenschwager
(74) *Attorney, Agent, or Firm* — Foley & Lardner LLP; Melissa El Menaouar; Joseph P. Meara

(57) ABSTRACT

A process for making a tertiary aminoalcohol compound is disclosed. The process comprises using an excess amount of a carbonyl compound in a condensation step between the carbonyl compound and a nitroalkane in the presence of a catalytic amount of a tertiary aminoalcohol compound, and conducting a hydrogenation/alkylation step to produce the tertiary aminoalcohol. The tertiary aminoalcohol compound used to catalyze the condensation step is preferably the same tertiary aminoalcohol compound produced in the hydrogenation/alkylation step. The process uses fewer steps than conventional processes.

20 Claims, No Drawings

PROCESS FOR MAKING TERTIARY AMINOALCOHOL COMPOUNDS

This application is a U.S. national phase of International Application No. PCT/US2012/046855, filed Jul. 16, 2012, which claims priority from U.S. Provisional Application No. 61/509,937, filed Jul. 20, 2011; the disclosures of both of these applications are incorporated herein by reference in their entireties.

FIELD OF THE INVENTION

The invention relates to an improved process for making tertiary aminoalcohol compounds.

BACKGROUND OF THE INVENTION

Tertiary aminoalcohol compounds play an important role in a variety of commercial and consumer products. For instance, they may be used as neutralizers in paints and coatings, in process water applications, and personal care and cosmetics formulations, as emulsifying agents, as corrosion inhibitors, e.g., in metalworking fluids, as resin solubilizers, foam catalysts, finish stabilizers, and/or as raw materials for chemical synthesis of other useful materials.

Tertiary aminoalcohol compounds are generally prepared on a commercial scale from nitroalkanes by a four step process. The condensation reaction (Henry Reaction) between aldehyde and nitroalkane forms the nitroalcohol. Catalytic reduction (hydrogenation) produces the corresponding aminoalcohol. A purification step (crystallization or distillation) eliminates impurity carryover to the final product. Finally a reductive alkylation (2nd hydrogenation) step produces the tertiary aminoalcohol.

It would be an advance in the art if new processes were developed that provided advantages over the known processes, such as reducing the number of process steps, increasing yield, and/or reducing manufacturing costs. Such an improved process is disclosed in U.S. Ser. No. 61/386,664, filed Sep. 27, 2010, the disclosure of which is incorporated herein by reference in its entirety.

It is further an object of the invention to provide such a process in which the overall cycle time of the process is reduced.

It is another object of the invention to provide such a process comprising the use of a catalyst for the Henry reaction.

It is still another object of the invention to provide such a process comprising the use of a catalyst for the Henry reaction in which the catalyst does not have to be removed from the reaction product.

SUMMARY OF THE INVENTION

The invention provides a process for making tertiary aminoalcohol compounds in which the overall cycle time of the process is reduced.

The invention further provides such a process comprising the use of a catalyst for the Henry reaction.

The invention also provides such a process in which the catalyst for the Henry reaction does not need to be removed from the reaction product.

Thus, the invention provides a process for making a tertiary aminoalcohol compound of formula I:

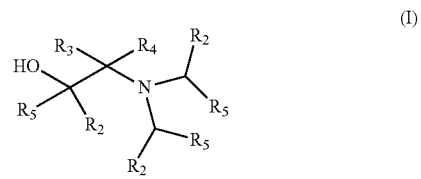

(I)

wherein each $R_2$ is independently H or $C_1$-$C_6$ alkyl;

each $R_5$ is independently H, $C_1$-$C_6$ alkyl, or $C_3$-$C_{12}$ cycloalkyl, or $R_2$ and $R_5$ together with the carbon to which they are attached form $C_3$-$C_{12}$ cycloalkyl;

each of $R_3$ and $R_4$ is independently $C_1$-$C_6$ alkyl, $C_3$-$C_{12}$ cycloalkyl, or —C(OH)$R_2R_5$, or $R_3$ and $R_4$ together with the carbon to which they are attached form $C_3$-$C_{12}$ cycloalkyl, Unless otherwise indicated, R, $R_1$, $R_2$, $R_3$, $R_4$, and $R_5$ in the formulas below have the definitions set forth above for formula I.

Preferably, all the $R_2$ groups are the same. Preferably all the $R_3$ groups are the same. Preferably, all the $R_4$ groups are the same. And preferably all the $R_5$ groups are the same.

The process comprises:

(a) reacting a nitroalkane compound of formula IV

(IV)

wherein R and $R_1$ are independently H, $C_1$-$C_6$ alkyl, or $C_3$-$C_{12}$ cycloalkyl;

with a molar excess (relative to the amount of nitroalkane compound) of a carbonyl compound of formula III

(III)

in the presence of a catalytic amount of a compound of formula I to form an intermediate product mixture comprising free carbonyl compound of formula III and a nitroalcohol compound of formula II

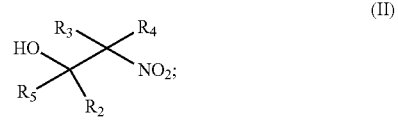

(II)

and (b) hydrogenating the intermediate product mixture in the presence of hydrogen and a hydrogenation catalyst such that the nitroalcohol compound of formula II and the free compound of formula III react therein to form the tertiary aminoalcohol compound of formula I.

In another aspect, the invention provides a process for making a compound of formula II

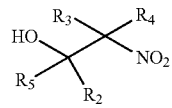
(II)

comprising reacting a compound of formula III

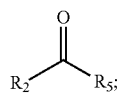
(III)

with a nitroalkane compound of formula IV

(IV)

wherein R and $R_1$ are independently H, $C_1$-$C_6$ alkyl, or $C_3$-$C_{12}$ cycloalkyl,
in the presence of a catalytic amount of a tertiary aminoalcohol compound of formula I

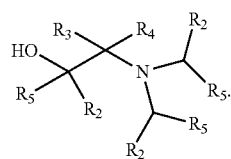
(I)

In yet another aspect, the invention provides a process for preparing a solution of a carbonyl compound of formula III

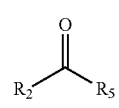
(III)

comprising providing a solution of a polymer formed from aldehyde or ketone monomers in a solvent system comprising an alcohol; and
reacting the polymer with an amount of a tertiary aminoalcohol compound of formula I sufficient to depolymerize the polymer

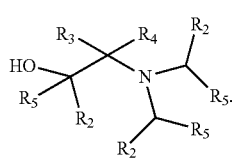
(I)

In still another aspect, the invention provides, a composition comprising a mixture of a carbonyl compound of formula III

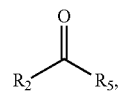
(III)

a nitroalkane compound of formula IV

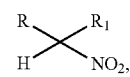
(IV)

and an amount of a tertiary aminoalcohol compound of formula I

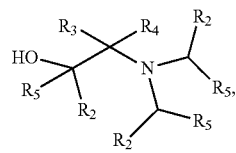
(I)

the amount of the tertiary aminoalcohol compound of formula I being less than the amount of either the carbonyl compound of formula III or the nitroalkane compound of formula IV, in an alcohol solvent, the composition being substantially free of a compound of nitroalcohol formula II

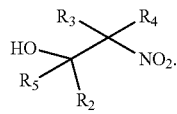
(II)

In still another aspect, the invention provides a composition that comprises a mixture of
a solvent,
a tertiary aminoalcohol compound of formula I (preferably in a catalytic amount)

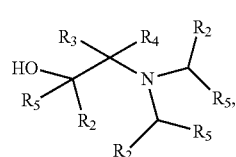
(I)

and either (a) a carbonyl compound of formula III

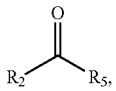

or (b) a nitroalkane compound of formula IV

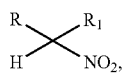

the composition being substantially free of a nitroalcohol compound of formula II

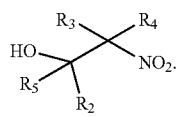

In still another aspect, the invention provides a process for making a tertiary aminoalcohol compound of formula I

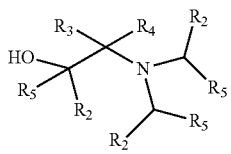

comprising (a) treating, in an alcohol solvent, a polymer formed from carbonyl monomers of formula III

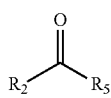

with (1) a catalytic amount of a tertiary aminoalcohol compound of formula I and (2) a compound of nitroalkane formula IV

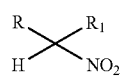

wherein R and $R_1$ are independently H, $C_1$-$C_6$ alkyl, or $C_3$-$C_{12}$ cycloalkyl, to produce an intermediate product mixture; and (b) hydrogenating the intermediate product mixture in the presence of hydrogen and a catalyst.

DETAILED DESCRIPTION OF THE INVENTION

In one aspect, the invention provides a process for making a tertiary aminoalcohol compound. The process exhibits various advantages over conventional processes. In particular, according to some embodiments, the invention can be conducted without the necessity of isolation and/or purification of the intermediate compounds, thus resulting in fewer process steps. In addition, in certain embodiments, the process of the invention results in formation of the desired product in higher yield than conventional systems. Further, certain embodiments of the process also result in additional cost savings, aside from the fixed cost savings by eliminating process steps and the savings from increased yield. Further, the process is more efficient, because overall cycle time is reduced. Moreover, the invention provides a catalyst for the Henry reaction that does not require removal from the reaction product.

It has been found that, surprisingly, a tertiary aminoalcohol compound of formula I can have two advantageous functions in the process of the invention. First, such a tertiary aminoalcohol compound can serve as a catalyst for the Henry reaction in which the carbonyl compound of formula III is reacted with the nitroalkane of formula IV to provide the nitroalcohol of formula II. In addition, where the carbonyl compound of formula III is originally in the form of a polymer, a catalytic amount of the tertiary aminoalcohol compound of formula I can be used to promote the depolymerization of the polymer to more rapidly provide a solution of the carbonyl-containing monomer of formula III. Advantageously, in such cases the presence of the tertiary aminoalcohol compound of formula I in the solution of the carbonyl monomer of formula III then acts as a catalyst in the subsequent Henry reaction when the nitroalkane compound of formula IV is added to make the nitroalcohol compound of formula II, without the need to separate out the depolymerization catalyst. In a particularly advantageous aspect of the invention, the tertiary aminoalcohol compound of formula I used as a catalyst in the Henry reaction, and preferably in both the depolymerization reaction and the Henry reaction, is the same tertiary aminoalcohol compound as the desired reaction product of the hydrogenation/alkylation of the nitroalcohol of formula II.

In one embodiment of the process, a catalytic amount of a compound of formula I is used to promote the depolymerization of a polymer formed from carbonyl-containing monomers, thereby making the carbonyl more accessible for subsequent reaction. Then, a nitroalkane compound is added, forming a mixture of carbonyl-containing compound(s), a catalytic amount of the compound of formula I, and the nitroalkane. When beginning the addition of nitroalkane, there is little or no nitroalcohol compound present. The nitroalkane subsequently reacts with the carbonyl compound, consuming the nitroalkane, and forms an intermediate product mixture including a nitroalcohol and free unreacted carbonyl compound. The compound of formula I, when used as a depolymerization catalyst, is also present during the subsequent reaction of carbonyl compound and nitroalkane, and serves as a catalyst in this reaction as well. The mixture is then hydrogenated/alkylated in the presence of hydrogen and a hydrogenation catalyst such that the hydrogen, the nitroalcohol compound and the remaining free carbonyl compound in the mixture react to form the desired tertiary aminoalcohol compound. In a preferred embodiment, the compound of formula I used as the depolymerization catalyst and Henry reaction catalyst is the same compound desired as the end product of the hydrogenation/alkylation reaction.

In certain embodiments, one or more additional tertiary amine catalysts different than the catalyst of formula I may be employed; such catalysts may require removal from the final product mixture.

The nitroalkane of the process is a compound of the formula IV:

wherein R and $R_1$ are independently H, $C_1$-$C_6$ alkyl, or $C_3$-$C_{12}$ cycloalkyl. In some embodiments, R and $R_1$ are both H. In some embodiments, R is H and $R_1$ is $C_1$-$C_6$ alkyl, alternatively $C_1$-$C_3$ alkyl, alternatively ethyl, or alternatively methyl. In some embodiments, R and $R_1$ are both independently $C_1$-$C_6$ alkyl. In some embodiments, both are n-propyl, alternatively ethyl, or alternatively methyl. In a particular embodiment, both of R and $R_1$ are methyl. In some embodiments, R and $R_1$ together with the carbon to which they are attached form $C_3$-$C_{12}$ cycloalkyl, alternatively $C_4$-$C_7$ cycloalkyl, or alternatively cyclohexyl. In some embodiments, the nitroalkane compound is nitromethane, nitroethane, 1-nitropropane, 2-nitropropane, or nitrocyclohexane.

The starting carbonyl compound of the process is a material of the formula III:

wherein $R_2$ is H or $C_1$-$C_6$ alkyl; and $R_5$ is H, $C_1$-$C_6$ alkyl, or $C_3$-$C_{12}$ cycloalkyl, or $R_2$ and $R_5$ together with the carbon to which they are attached form $C_3$-$C_{12}$ cycloalkyl. In some embodiments, $R_2$ and $R_5$ are both H. In some embodiments, $R_2$ is H and $R_5$ is $C_1$-$C_6$ alkyl, alternatively $C_1$-$C_3$ alkyl, alternatively ethyl, or alternatively methyl. In some embodiments, $R_2$ and $R_5$ are both independently $C_1$-$C_6$ alkyl, alternatively they are independently $C_1$-$C_3$ alkyl. In some embodiments, $R_2$ is H and $R_5$ is $C_3$-$C_{12}$ cycloalkyl, alternatively $C_4$-$C_7$ cycloalkyl, or alternatively cyclohexyl. In some embodiments, $R_2$ and $R_5$ together with the carbon to which they are attached form $C_3$-$C_{12}$ cycloalkyl, alternatively $C_4$-$C_7$ cycloalkyl, or alternatively cyclohexyl. In some embodiments, the compound is formaldehyde, i.e., both of $R_2$ and $R_5$ are hydrogen. In a preferred embodiment of the invention, the formaldehyde used in the reaction is derived from paraformaldehyde by depolymerization of paraformaldehyde in an appropriate solvent, preferably an alcohol solvent, in the presence of a catalytic amount of a compound of formula I, as described below. Most preferably, the alcohol solvent is methanol.

In the invention process, the carbonyl compound of formula III and the nitroalkane of formula IV undergo a condensation reaction catalyzed by the catalytic amount of a compound of formula I, which in one aspect of the invention can be present in the solution of the compound of formula III produced via the catalyzed depolymerization step. The carbonyl compound of formula III reacts in the presence of the catalytic amount of the compound of formula I with the nitroalkane of formula IV to produce a nitroalcohol compound, as a component of, in certain embodiments of the invention, the intermediate product mixture.

The inventors have found that, surprisingly, the presence in the starting reaction mixture of a catalytic amount of a compound of formula I, which preferably is the desired end product, facilitates the reaction between the compound of formula III and the compound of formula IV. In addition, where the carbonyl compound of formula III is obtained as a polymer, e.g., paraformaldehyde, the compound of formula I facilitates depolymerization and dissolution of the compound of formula III, particularly in the presence of an alcohol solvent, thereby increasing the availability of the carbonyl compound of formula III for subsequent reaction with the compound of formula IV. In a particularly preferred example, in which paraformaldehyde is the source of the carbonyl compound of formula III and the solvent is methanol, the presence of a catalytic quantity of a compound of formula I facilitates the depolymerization of the paraformaldehyde in the methanol solvent, thereby facilitating the subsequent reaction of the compound of formula III with the compound of formula IV. This also substantially reduces the cycle time of the reaction, because paraformaldehyde can dissolve as much as eight times faster in methanol when a catalytic amount of a compound of formula I is present than in the absence of such a compound.

Another advantage of the invention is that when a catalytic amount of a compound of formula I is used to facilitate the depolymerization to produce the compound of formula III, the compound of formula I will, under typical conditions, remain in the reaction mixture and be available to catalyze the subsequent Henry reaction.

As an example of a typical process starting with paraformaldehyde, a polymer of a carbonyl-containing monomer is dissolved in the presence of a compound of formula I. In one example, the polymer compound can be paraformaldehyde, the compound of formula I can be 2-dimethylamino-2-methyl-1-propanol ("DMAMP"), which can be added as an 80% aqueous solution, and the solvent can be methanol. The polymer and the solvent can be present in a ratio of about 1:1 to about 2:1 by weight. The compound of formula I can be present in an amount of about 0.1%-15%, preferably about 0.5-12%, and more preferably about 1-10%, of the weight of the polymer compound.

The depolymerization, which occurs upon treating the carbonyl monomers of formula III, can take place at a temperature of about 45° C.-65° C., or of about of about 50° C.-60° C., preferably about 55° C., for a period of about fifteen minutes to about two hours, depending on the temperature and the amount of catalyst used. Once depolymerization is achieved, the resulting unpolymerized carbonyl compound may be reacted with the nitroalkane. Of course, depolymerization is unnecessary when the starting carbonyl compound is substantially monomeric.

Thus, after depolymerization, the temperature of the mixture can be raised to about 65° C., and a nitroalkane can be added in an amount of about 1 molar equivalent of the nitroalkane to 3 molar equivalents of the monomer (carbonyl compound). An excess of 2 molar equivalents of the monomer (carbonyl compound) is necessary to prepare compounds of Formula I such as DMAMP, so although larger excesses can be used, additional carbonyl compound is not preferred. One suitable nitroalkane is 2-nitropropane.

The nitroalkane can be added slowly, i.e., over a period of 1-4 hours, so as to maintain the temperature of the reaction mixture.

Various additional base catalysts may be used in the condensation reaction in addition to the compound of formula I. These include, for instance, inorganic bases (e.g., sodium hydroxide, calcium hydroxide) or other organic tertiary amines, such as, for example triethylamine. The concentration of the additional basic catalyst may be in the range of, for example, 0.1 to 2.0 percent by weight, based on the weight of the nitroalkane.

A solvent may be used in the Henry, or condensation, reaction. Suitable solvents are those that do not substantially interfere with the formation of the desired product. Examples include, for instance, lower alcohols such as methanol, ethanol, n-propanol, and isopropanol, and mixtures thereof.

The same conditions and ratios are typically used for the Henry reaction when the carbonyl compound is obtained in unpolymerized form. However, the catalytic amount of the compound of formula I in step (a) may be in the range of about 0.01-10.0 wt percent of the amount of the compound of formula III. More preferably, the catalytic amount of the compound of formula I in step (a) is about 3-7 wt percent of the total amount of the compound of formula III.

The nitroalcohol formed in the condensation reaction between the nitroalkane and the carbonyl compound may be represented by the following formula II:

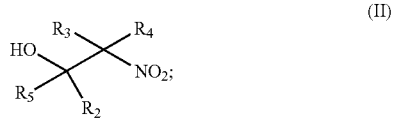

wherein $R_2$ and $R_5$ are as defined above (including the various embodiments thereof), and $R_3$ and $R_4$ are independently $C_1$-$C_6$ alkyl, $C_3$-$C_{12}$ cycloalkyl, or —$C(OH)R_2R_5$, or $R_3$ and $R_4$ together with the carbon to which they are attached form $C_3$-$C_{12}$ cycloalkyl.

In some embodiments, $R_3$ and $R_4$ in the formula II compounds are each independently $C_1$-$C_6$ alkyl, or they are independently $C_1$-$C_3$ alkyl. In some embodiments, both are n-propyl, alternatively ethyl, or alternatively methyl. In some embodiments, $R_3$ and $R_4$ together with the carbon to which they are attached form $C_3$-$C_{12}$ cycloalkyl, alternatively $C_4$-$C_7$ cycloalkyl, or alternatively cyclohexyl.

In some embodiments, $R_3$ in the formula II compounds is —$C(OH)R_2R_5$, and $R_2$ and $R_5$ are both H. In some embodiments, $R_3$ is —$C(OH)R_2R_5$, $R_2$ is H and $R_5$ is $C_1$-$C_6$ alkyl, alternatively $C_1$-$C_3$ alkyl, alternatively ethyl, or alternatively methyl. In some embodiments, $R_3$ is —$C(OH)R_2R_5$, $R_2$ is H and $R_5$ is $C_3$-$C_{12}$ cycloalkyl, alternatively $C_4$-$C_7$ cycloalkyl, or alternatively cyclohexyl. In some embodiments, $R_3$ is —$C(OH)R_2R_5$, and $R_2$ and $R_5$ are both independently $C_1$-$C_6$ alkyl, alternatively they are independently $C_1$-$C_3$ alkyl. In some embodiments, $R_3$ is —$C(OH)R_2R_5$, and $R_2$ and $R_5$ together with the carbon to which they are attached form $C_3$-$C_{12}$ cycloalkyl, alternatively $C_4$-$C_7$ cycloalkyl, or alternatively cyclohexyl.

In some embodiments, $R_3$ in the formula II compounds is —$C(OH)R_2R_5$ and $R_4$ is $C_1$-$C_6$ alkyl, alternatively $C_1$-$C_3$ alkyl, alternatively ethyl, or alternatively methyl. An important aspect of the invention process is that the intermediate product mixture that contains the formula II nitroalcohol also contains free carbonyl compound of formula III. The free carbonyl compound functions, in the hydrogenation/alkylation step of the process, to react with the nitroalcohol to form the desired tertiary aminoalcohol.

In order to provide an intermediate product mixture that contains free carbonyl compound, according to the invention, an amount of the carbonyl compound in excess of that required for completion of the condensation reaction described above is used. As a result, the unreacted formula III carbonyl compound remains present in the intermediate product mixture and is therefore available for the hydrogenation/alkylation step.

In order to achieve reasonable yield and to reduce formation of undesired byproducts, it is preferred that a sufficient amount of formula III carbonyl compound be used in the condensation reaction step such that, following completion of that reaction, the intermediate product mixture contains at least 2 moles of free formula III carbonyl compound per mole of formula II nitroalcohol compound in the intermediate product mixture.

The amount of the carbonyl compound to be used in the condensation step to provide such excess can be readily calculated by those skilled in the art, and will depend primarily on the number of hydrogens in the nitroalkane compound that are available for the condensation reaction. By way example, 2-nitropropane will generally react with one mole of carbonyl compound in the condensation reaction. Therefore, in order to provide an intermediate product mixture that contains at least 2 moles of free carbonyl compound per mole of nitroalcohol, at least 3 moles of the carbonyl compound per mole of nitroalkane may be used in the condensation reaction. Similarly, for nitromethane, at least five equivalents of the carbonyl compound may be used for each equivalent of the nitroalkane. For nitroethane and 1-nitropropane, at least four equivalents of the carbonyl compound may be used.

Formation of the desired tertiary aminoalcohol is achieved by hydrogenating/alkylating the intermediate product mixture in the presence of hydrogen and a hydrogenation catalyst such that the nitroalcohol compound of formula II, the free carbonyl compound of formula III, and the hydrogen react to yield the tertiary aminoalcohol.

The hydrogenation/alkylation reaction is carried out in the presence of hydrogen gas in combination with a hydrogenation catalyst, for example, Raney nickel or a platinum or palladium based catalyst (Pt or Pd in elemental form or as oxides, with or without supports, e.g., carbon). Preferred is Raney nickel.

Hydrogenation/alkylation conditions may be readily determined by those skilled in the art. By way of example, a temperature range of about 30-170° C., alternatively about 100-120° C., and a pressure of about 100-1000 psi (690 kPa-6900 kPa) may be used. The concentration of catalyst may vary, and is typically between about 1 and 25 weight percent, based on the nitroalcohol. A solvent may be used, such as methanol. The hydrogenation reaction is continued until the desired amount of product is formed, preferably to completion, which is typically 1 to 12 hours.

Optionally, the process of the invention may further include a final aldehyde/ketone trim step following the hydrogenation/alkylation. In this optional step, additional carbonyl compound of formula III is slowly fed into the hydrogenation/alkylation product mixture, and the resultant mixture held at temperature for an additional time, e.g., 1-3 hours. The trim step may help further increase the alkylation to desired product, thus potentially increasing overall product yield.

Preferably, following the hydrogenation/alkylation reaction (e.g., step b)), the intermediate product mixture contains at least 0.5 percent, alternatively at least 5 percent, alternatively at least 10 percent, or alternatively at least 20 percent by weight of the desired tertiary aminoalcohol. The tertiary aminoalcohol may be filtered to separate it from the hydrogenation/alkylation catalyst. Additional workup may be carried out, such as vacuum removal of excess solvent, and/or distillation of the tertiary aminoalcohol.

The tertiary aminoalcohol prepared according to the invention is a compound of the formula I:

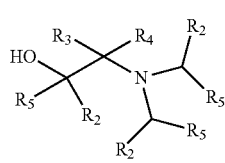

wherein $R_2$ is H or $C_1$-$C_6$ alkyl; $R_5$ is H, $C_1$-$C_6$ alkyl, or $C_3$-$C_{12}$ cycloalkyl, or $R_2$ and $R_5$ together with the carbon to which they are attached form $C_3$-$C_{12}$ cycloalkyl; $R_3$ and $R_4$ are independently $C_1$-$C_6$ alkyl, $C_3$-$C_{12}$ cycloalkyl, or —C(OH)$R_2R_5$, or $R_3$ and $R_4$ together with the carbon to which they are attached form $C_3$-$C_{12}$ cycloalkyl.

In some embodiments of the invention, $R_2$ and $R_5$ in the formula I compounds are both H. In some embodiments, $R_2$ is H and $R_5$ is $C_1$-$C_6$ alkyl, alternatively $C_1$-$C_3$ alkyl, alternatively ethyl, or alternatively methyl. In some embodiments, $R_2$ and $R_5$ are both independently $C_1$-$C_6$ alkyl, alternatively they are independently $C_1$-$C_3$ alkyl.

In some embodiments, $R_2$ is H and $R_5$ is $C_3$-$C_{12}$ cycloalkyl, alternatively $C_4$-$C_7$ cycloalkyl, or alternatively cyclohexyl. In some embodiments, $R_2$ and $R_5$ together with the carbon to which they are attached form $C_3$-$C_{12}$ cycloalkyl, alternatively $C_4$-$C_7$ cycloalkyl, or alternatively cyclohexyl.

In some embodiments, $R_3$ and $R_4$ in the formula I compounds are each independently $C_1$-$C_6$ alkyl, or they are independently $C_1$-$C_3$ alkyl. In some embodiments, both are n-propyl, alternatively ethyl, or alternatively methyl. In some embodiments, $R_3$ and $R_4$ together with the carbon to which they are attached form $C_3$-$C_{12}$ cycloalkyl, alternatively $C_4$-$C_7$ cycloalkyl, or alternatively cyclohexyl. In other embodiments, $R_3$ and $R_4$ are each —C(OH)$R_2R_5$.

In some embodiments, $R_3$ in the formula I compounds is —C(OH)$R_2R_5$, and $R_2$ and $R_5$ are both H. In some embodiments, $R_3$ is —C(OH)$R_2R_5$, $R_2$ is H and $R_5$ is $C_1$-$C_6$ alkyl, alternatively $C_1$-$C_3$ alkyl, alternatively ethyl, or alternatively methyl. In some embodiments, $R_3$ is —C(OH)$R_2R_5$, $R_2$ is H and $R_5$ is $C_3$-$C_{12}$ cycloalkyl, alternatively $C_4$-$C_7$ cycloalkyl, or alternatively cyclohexyl. In some embodiments, $R_3$ is —C(OH)$R_2R_5$, and $R_2$ and $R_5$ are both independently $C_1$-$C_6$ alkyl, alternatively they are independently $C_1$-$C_3$ alkyl. In some embodiments, $R_3$ is —C(OH)$R_2R_5$, and $R_2$ and $R_5$ together with the carbon to which they are attached form $C_3$-$C_{12}$ cycloalkyl, alternatively $C_4$-$C_7$ cycloalkyl, or alternatively cyclohexyl.

In some embodiments, $R_3$ in the formula I compounds is —C(OH)$R_2R_5$ and $R_4$ is $C_1$-$C_6$ alkyl, alternatively $C_1$-$C_3$ alkyl, alternatively ethyl, or alternatively methyl.

Preferred compounds of formula I include: 2-(dimethylamino)-2-methyl-1-propanol, N,N-dimethyltris(hydroxymethyl)aminomethane, 2-(dimethylamino)-2-ethylpropane-1,3-diol, 2-(dimethylamino)-2-methylpropane-1,3-diol or 1-(dimethylamino)cyclohexyl-methanol.

Tertiary aminoalcohols prepared according to the invention may be used in a variety of applications. For instance, they may be used as neutralizers in paints and coatings, process water applications, and personal care and cosmetics formulations, as emulsifying agents, as corrosion inhibitors, e.g., in metalworking fluids, as resin solubilizers, foam catalysts, finish stabilizers, and/or as raw materials for chemical synthesis of other useful materials.

"Alkyl" as used in this specification encompasses straight and branched chain aliphatic groups having the indicated number of carbon atoms. If no number is indicated (e.g., aryl-alkyl-), then 1-6 alkyl carbons are contemplated. Preferred alkyl groups include, without limitation, methyl, ethyl, propyl, isopropyl, butyl, isobutyl, sec-butyl, tert-butyl, pentyl, and hexyl. Unless otherwise indicated, the alkyl group is optionally substituted with 1, 2, or 3, preferably 1 or 2, more preferably 1, substituents that are compatible with the syntheses described herein. Such substituents include, but are not limited to, nitro, halogen, carboxylic acids (e.g., $C_0$-$C_6$—COOH), and $C_2$-$C_6$ alkene. Unless otherwise indicated, the foregoing substituent groups are not themselves further substituted.

The term "cycloalkyl" refers to saturated and partially unsaturated cyclic hydrocarbon groups having the indicated number of ring carbon atoms. If no number is specified, then 3 to 12 carbons, preferably 3 to 8 carbons, and more preferably 3 to 7 carbons, are contemplated. Preferred cycloalkyl groups include, without limitation, cyclopropyl, cyclobutyl, cyclopentyl, cyclopentenyl, cyclohexyl, cyclohexenyl, cycloheptyl, and cyclooctyl. Unless otherwise indicated, the cycloalkyl group is optionally substituted with 1, 2, or 3, preferably 1 or 2, more preferably 1, substituents that are compatible with the syntheses described herein. Such substituents include, but are not limited to, $C_1$-$C_6$ alkyl, nitro, halogen, carboxylic acids (e.g., $C_0$-$C_6$—COOH), and $C_2$-$C_6$ alkene. A preferred substituent is $C_1$-$C_6$ alkyl. Unless otherwise indicated, the foregoing substituent groups are not themselves further substituted.

The following examples are illustrative of the invention but are not intended to limit its scope. Unless otherwise indicated, the ratios, percentages, parts, and the like used herein are by weight.

EXAMPLES

Example 1

Preparation of
2-(dimethylamino)-2-methyl-1-propanol (DMAMP)

Conversion of 2-nitropropane (2-NP) to 2-nitro-2-methyl-1-propanol (NMP)

3 equivalents of methyl formcel are charged to a reaction flask. The reaction is catalyzed with 0.65 mole % triethylamine (TEA), which is added to the methyl formcel. The methyl formcel/TEA mixture is heated to 85° C. and the 2-NP is added incrementally over approximately 2 hours. The reaction is followed by a one hour hold period at 85° C. to complete conversion. At 60° C., a 2 hour hold time is needed for complete conversion.

Conversion of NMP to DMAMP

NMP is converted to DMAMP by a stepwise reduction with hydrogen to form 2-amino-2-methyl-1-propanol (AMP). The AMP is not isolated but reacted in situ with the excess formaldehyde (from step 1) so that DMAMP is continuously being formed throughout the hydrogenation. Upon completion, and depending on the temperature during the NMP feed, the temperature is increased to promote methylation. GC scans of in-process samples show multiple peaks. These various compounds are not impurities but rather intermediates, including the monooxazolidine of AMP, the monomethylated AMP, and the monooxazolidine of MMAMP. After 1 hour at elevated temperature, a methyl formcel trim is slowly fed to the autoclave. After the methyl formcel trim, the reactor is held at temperature for an additional hour to complete the methylation.

For higher yield and product purity, the NMP feed is preferably carried out at the lowest practical temperature. To simplify the process, all autoclave steps are carried out at 100° C. For further simplification of the process, the NMP may be fed at 65° C. and cooling water shut off at different points to allow the reaction exotherm to increase the temperature prior to the methyl formcel trim (to complete the methylation).

Example 2

Depolymerization of Paraformaldehyde to Formaldehyde a. (Comparative) Fifty grams of methanol is mixed with 50 grams of paraformaldehyde at 55° C. and no 2-(dimethylamino)-2-methyl-1-propanol. After 120 minutes the mixture is still a white suspension.
b. Fifty grams of methanol is mixed with 50 grams of paraformaldehyde at 55° C. and five grams of an 80% solution of 2-(dimethylamino)-2-methyl-1-propanol in water. After 15 minutes only a few crystals remained in the reaction mixture and after 75 minutes the crystals had disappeared and the mixture had only a slight turbidity.
c. Fifty grams of methanol is mixed with 50 grams of paraformaldehyde at 55° C. and 0.1 grams of an 80% solution of 2-(dimethylamino)-2-methyl-1-propanol in water. After 60 minutes most of the crystals in the reaction mixture had dissolved and after 120 minutes the crystals had disappeared and the mixture had only a slight turbidity.

Example 3

Preparation of 2-nitro-2-methyl-1-propanol

A 500 ml, 3-necked round bottom flask equipped with a hot water bath, magnetic stirrer, addition funnel, and thermometer was charged with 184 grams of methylformcel (55% formaldehyde by weight in methanol) and 10.1 grams of an 80% solution of 2-(dimethylamino)-2-methyl-1-propanol in water with stirring. The flask and its contents were brought to 65° C. and stabilized. To the flask 100 g of 2-nitropropane was added slowly over a period of 5 minutes, the temperature of the flask contents being maintained between 65° C. and 71° C. using a water bath. A sample of the flask contents was taken immediately after completion of the addition of the 2-nitropropane, and then at 1 hour, 2 hours, and 3 hours after the initial sample. The samples were analyzed by gas chromatography. The initial sample showed that the reaction was about 97% complete, with 2% of 2-nitropropane remaining. The other samples showed complete reaction.

The Henry reaction was conducted with 3 equivalents of formaldehyde. Thus, the 2-nitro-2-methyl-1-propanol intermediate product mixture prepared immediately above may, without the addition of more formaldehyde, be carried on to produce 2-(dimethylamino)-2-methyl-1-propanol by hydrogenating/alkylating the intermediate product mixture in the presence of hydrogen and a hydrogenation catalyst such that the 2-nitro-2-methyl-1-propanol, the remaining formaldehyde, and the hydrogen react to yield 2-(dimethylamino)-2-methyl-1-propanol, as demonstrated above in Example 1.

In some embodiments, it may be useful to provide mixtures of the reactants prior to reaction at various stages of the process disclosed herein. Thus in one embodiment of the invention, a composition comprises a mixture of a compound of formula III

a compound of formula IV

and a catalytic amount of a compound of formula I

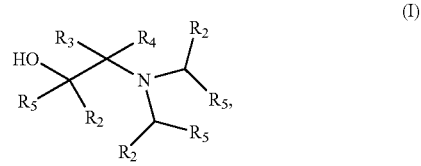

the amount of the compound of formula I being less than the amount of either the compound of formula III or the compound of formal IV, in an alcohol solvent, the composition being substantially free of a compound of formula II. The mixture will be substantially free of the compound of formula II until the reaction between the compound of formula III and the compound of formula IV, as catalyzed by the compound of formula I, commences at an elevated temperature.

In another aspect, of the invention, a composition comprises a mixture of a solvent,
a compound of formula I

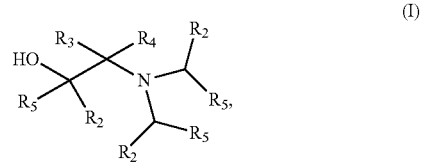

and either
(a) a compound of formula III

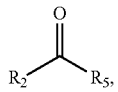
(III)

or
(b) a compound of formula IV

(IV)

the composition being substantially free of a compound of formula II

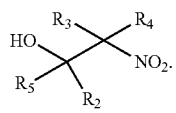
(II)

Such a composition of formula I and formula IV may exist if the overall reaction is carried out in a sequence in which the compounds of formula I and formula IV are first mixed together, then the carbonyl-containing polymer is added, so that the depolymerization reaction to form the compound of formula III and the subsequent condensation reaction with the compound of formula IV to form the compound of formula II occur almost simultaneously in the same vessel.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process for making a compound of formula I:

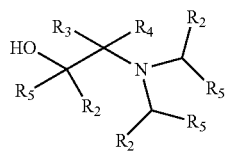
(I)

wherein
each $R_2$ is independently H or $C_1$-$C_6$ alkyl;
each $R_5$ is independently H, $C_1$-$C_6$ alkyl, or $C_3$-$C_{12}$ cycloalkyl, or $R_2$ and $R_5$ together with the carbon to which they are attached form $C_3$-$C_{12}$ cycloalkyl; and
$R_3$ and $R_4$ are independently $C_1$-$C_6$ alkyl, $C_3$-$C_{12}$ cycloalkyl, or —C(OH)$R_2R_5$, or $R_3$ and $R_4$ together with the carbon to which they are attached form $C_3$-$C_{12}$ cycloalkyl, the process comprising:
(a) reacting a compound of formula III

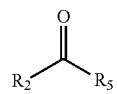
(III)

with a compound of formula IV

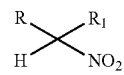
(IV)

wherein R and $R_1$ are independently H, $C_1$-$C_6$ alkyl, or $C_3$-$C_{12}$ cycloalkyl, in the presence of a catalytic amount of the compound of formula I to produce an intermediate product mixture comprising free compound of formula III and a nitroalcohol compound of formula II

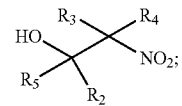
(II)

and
(b) hydrogenating the intermediate product mixture in the presence of hydrogen and a catalyst.

2. The process of claim 1 wherein the intermediate product mixture of step (a) comprises at least two moles of free carbonyl compound of formula III per mole of nitroalcohol compound of formula II.

3. The process according to claim 2 wherein additional carbonyl compound of formula III is added following step (b).

4. The process according to claim 2 wherein $R_3$ and $R_4$ are each independently $C_1$-$C_3$ alkyl.

5. The process according to claim 2 wherein $R_2$ and $R_5$ are H.

6. The process according to claim 2 wherein $R_3$ and $R_4$ are each meth.

7. The process according to claim 2 wherein all $R_2$ groups are the same and all $R_5$ groups are the same.

8. The process of claim 1 wherein additional carbonyl compound of formula III is added following step (b).

9. The process of claim 1 wherein $R_3$ and $R_4$ are each independently $C_1$-$C_3$ alkyl.

10. The process of claim 1 wherein $R_3$ and $R_4$ are each —C(OH)$R_2R_5$.

11. The process of claim 1 wherein $R_3$ is —C(OH)$R_2R_5$ and $R_4$ is $C_1$-$C_6$ alkyl.

12. The process of claim 1 wherein $R_3$ and $R_4$ together with the carbon to which they are attached form $C_3$-$C_{12}$ cycloalkyl.

13. The process of claim 1 wherein $R_2$ and $R_5$ are H.

14. The process of claim 1, further comprising depolymerizing paraformaldehyde to generate at least a portion of the carbonyl compound of formula III.

15. The process of claim 14 wherein said depolymerization is catalyzed by a compound of formula I.

16. The process according to claim 1 wherein all $R_2$ groups are the same and all $R_5$ groups are the same.

17. A process for preparing a solution of a compound of formula III

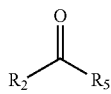
(III)

wherein each $R_2$ is independently H or $C_1$-$C_6$ alkyl;
each $R_5$ is independently H, $C_1$-$C_6$ alkyl, or $C_3$-$C_{12}$ cycloalkyl, or $R_2$ and $R_5$ together with the carbon to which they are attached form $C_3$-$C_{12}$ cycloalkyl;
the process comprising
providing a solution of a polymer formed from aldehyde or ketone monomers in a solvent system comprising an alcohol; and
reacting the polymer with an amount of a compound of formula I sufficient to depolymerize the polymer

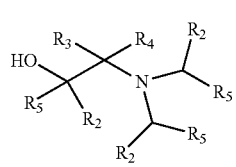
(I)

wherein $R_2$ and $R_5$ are as described above and $R_3$ and $R_4$ are independently $C_1$-$C_6$ alkyl, $C_3$-$C_{12}$ cycloalkyl, or —C(OH)$R_2R_5$, or $R_3$ and $R_4$ together with the carbon to which they are attached form $C_3$-$C_{12}$ cycloalkyl.

18. A composition comprising a mixture of
a compound of formula III

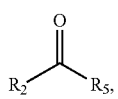
(III)

a compound of formula IV

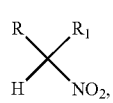
(IV)

and a catalytic amount of a compound of formula I

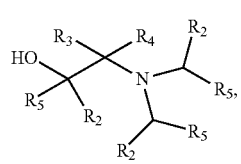
(I)

the catalytic amount of the compound of formula I being less than the amount of either the compound of formula III or the compound of formula IV, in an alcohol solvent, the composition being substantially free of a compound of formula II

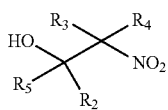
(II)

wherein R and $R_1$ are independently $C_1$-$C_6$ alkyl or $C_3$-$C_{12}$ cycloalkyl;
each $R_2$ is independently H or $C_1$-$C_6$ alkyl;
each $R_5$ is independently H, $C_1$-$C_6$ alkyl, or $C_3$-$C_{12}$ cycloalkyl, or $R_2$ and $R_5$ together with the carbon to which they are attached form $C_3$-$C_{12}$ cycloalkyl; and
$R_3$ and $R_4$ are independently $C_1$-$C_6$ alkyl or $C_3$-$C_{12}$ cycloalkyl, or $R_3$ and $R_4$ together with the carbon to which they are attached form $C_3$-$C_{12}$ cycloalkyl.

19. A composition consisting of a mixture of
a solvent,
a compound of formula I

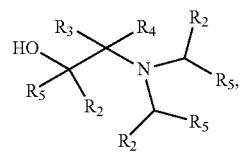
(I)

and either
(a) a compound of formula III

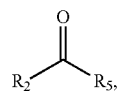
(III)

or
(b) a compound of formula IV

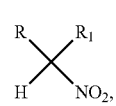
(IV)

the composition being substantially free of a compound of formula II

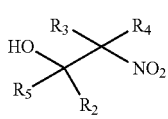
(II)

wherein
R and $R_1$ are independently $C_1$-$C_6$ alkyl, or $C_3$-$C_{12}$ cycloalkyl;
each $R_2$ is independently H or $C_1$-$C_6$ alkyl;

each $R_5$ is independently H, $C_1$-$C_6$ alkyl, or $C_3$-$C_{12}$ cycloalkyl, or $R_2$ and $R_5$ together with the carbon to which they are attached form $C_3$-$C_{12}$ cycloalkyl; and $R_3$ and $R_4$ are independently $C_1$-$C_6$ alky or $C_3$-$C_{12}$ cycloalkyl, or $R_3$ and $R_4$ together with the carbon to which they are attached form $C_3$-$C_{12}$ cycloalkyl.

20. A process for making a compound of formula I:

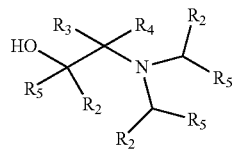
(I)

wherein
each $R_2$ is independently H or $C_1$-$C_6$ alkyl;
each $R_5$ is independently H, $C_1$-$C_6$ alkyl, or $C_3$-$C_{12}$ cycloalkyl, or $R_2$ and $R_5$ together with the carbon to which they are attached form $C_3$-$C_{12}$ cycloalkyl; and
$R_3$ and $R_4$ are independently $C_1$-$C_6$ alkyl, $C_3$-$C_{12}$ cycloalkyl, or —C(OH)$R_2R_5$, or $R_3$ and $R_4$ together with the carbon to which they are attached form $C_3$-$C_{12}$ cycloalkyl, the process comprising:
(a) treating, in an alcohol solvent, a polymer formed from monomers of formula III

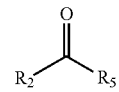
(III)

with (1) a catalytic amount of the compound of formula I and (2) a compound of formula IV

(IV)

wherein R and $R_1$ are independently H, $C_1$-$C_6$ alkyl, or $C_3$-$C_{12}$ cycloalkyl, to produce an intermediate product mixture; and
(b) hydrogenating the intermediate product mixture in the presence of hydrogen and a catalyst.

* * * * *

UNITED STATES PATENT AND TRADEMARK OFFICE
CERTIFICATE OF CORRECTION

PATENT NO. : 9,663,443 B2  
APPLICATION NO. : 14/233328  
DATED : May 30, 2017  
INVENTOR(S) : David W. Moore, Christian Spieker and John D. Gummere Page 1 of 1

It is certified that error appears in the above-identified patent and that said Letters Patent is hereby corrected as shown below:

In the Claims

Claim 6, Column 16, Line 48 should read:  
each methyl.

Signed and Sealed this  
Twenty-second Day of April, 2025

Coke Morgan Stewart  
*Acting Director of the United States Patent and Trademark Office*